United States Patent
Cazenave

(10) Patent No.: US 11,666,340 B2
(45) Date of Patent: *Jun. 6, 2023

(54) ADJUSTABLE VASCULAR RING AND IMPLANTABLE KIT COMPRISING SUCH A RING

(71) Applicant: MEDICAL INNOVATION DEVELOPPEMENT, Dardilly (FR)

(72) Inventor: Ludovic Cazenave, Dardilly (FR)

(73) Assignee: MEDICAL INNOVATION DEVELOPPEMENT, Dardilly (FR)

( * ) Notice: Subject to any disclaimer, the term of this patent is extended or adjusted under 35 U.S.C. 154(b) by 684 days.

This patent is subject to a terminal disclaimer.

(21) Appl. No.: 16/630,002

(22) PCT Filed: Jul. 11, 2018

(86) PCT No.: PCT/IB2018/000870
§ 371 (c)(1),
(2) Date: Jan. 10, 2020

(87) PCT Pub. No.: WO2019/012331
PCT Pub. Date: Jan. 17, 2019

(65) Prior Publication Data
US 2021/0113209 A1    Apr. 22, 2021

Related U.S. Application Data

(63) Continuation of application No. 15/647,329, filed on Jul. 12, 2017, now Pat. No. 10,568,633.

(51) Int. Cl.
*A61B 17/12*    (2006.01)
*A61B 17/135*   (2006.01)
*A61B 17/00*    (2006.01)

(52) U.S. Cl.
CPC ........ *A61B 17/12* (2013.01); *A61B 17/12009* (2013.01); *A61B 17/12013* (2013.01); *A61B 17/135* (2013.01); *A61B 2017/00557* (2013.01)

(58) Field of Classification Search
CPC .............. A61B 17/12; A61B 17/12009; A61B 17/12013; A61B 17/12099;
(Continued)

(56) References Cited

U.S. PATENT DOCUMENTS 7,500,944 B2 *   3/2009  Byrum ................. A61F 5/003
                                                         600/37
9,730,698 B2 *   8/2017  Cazenave ........ A61B 17/12009
(Continued)

FOREIGN PATENT DOCUMENTS

EP      0 196 837      10/1986
WO      88/05290        7/1988
(Continued)

*Primary Examiner* — Todd J Scherbel
(74) *Attorney, Agent, or Firm* — Clark & Brody LP

(57) ABSTRACT

Ring comprising:
an outer belt (3) equipped with closing means (7) for closing the ring (1) around a duct (2);
an inner chamber (4) that can be inflated and deflated;
a flexible inflation/deflation tube (5);
wherein the lips have contact surfaces facing each other, the closing means comprising at least one perforation arranged on the contact surface of a first of the two lips and at least one protrusion protruding from the contact surface of a second of the two lips, the protrusion and the perforation being configured so that the protrusion is retained in the perforation by fitting, the fitting being selected to be released in the event of overpressure in the ring.

12 Claims, 3 Drawing Sheets

(58) Field of Classification Search
CPC ........ A61B 17/12109; A61B 17/12113; A61B 17/12131; A61B 17/12136; A61B 17/132; A61B 17/1322; A61B 17/135; A61B 17/1355; A61B 2017/12004
See application file for complete search history.

(56) References Cited

U.S. PATENT DOCUMENTS

| | | | |
|---|---|---|---|
| 10,568,633 B2 * | 2/2020 | Cazenave | ............... A61B 17/12 |
| 2004/0267288 A1 | 12/2004 | Byrum | |
| 2008/0097947 A1 | 4/2008 | Stich et al. | |
| 2013/0304113 A1 * | 11/2013 | Eikman | ............... A61B 17/1322 |
| | | | 606/203 |

FOREIGN PATENT DOCUMENTS

| | | |
|---|---|---|
| WO | 2010/102661 | 9/2010 |
| WO | 2017/214644 | 12/2017 |

\* cited by examiner

ADJUSTABLE VASCULAR RING AND IMPLANTABLE KIT COMPRISING SUCH A RING

TECHNICAL FIELD

The field of the invention is that of medical devices that can be implanted by surgical route around a biological duct, in particular a vessel and more particularly a blood vessel such as the portal vein, in order to allow adjustment of the diameter of the duct and therefore of the flow rate of a fluid (blood) capable of circulating therein.

These implantable medical devices are more precisely vascular rings that can be inflated and deflated using a fluid, so as to adjust their inner diameter and thus the inner diameter of the ducts/vessels around which they are intended to be implanted.

The invention also relates to the kit that can be implanted by surgical route and allow control of the inner diameter of a vessel and, as a result, the flow rate of a fluid circulating therein.

TECHNOLOGICAL BACKGROUND OF THE INVENTION

It is known to implant medical devices constituted by inflating banding rings, around blood vessels of patients in order to restrict blood flow, for example on the pulmonary arteries. This is the subject of the patent application US2008/0097947A which discloses an annular banding device for the pulmonary artery, comprising an inflating banding ring intended to be put in place around the pulmonary artery of the patient, an inflation tube connecting the banding ring to an insufflating button. The banding ring is generally C-shaped and comprises an external thin rigid silicone layer and an internal thin silicone layer, forming an inflating balloon. The rigid silicone external layer or wall extends into the end zone corresponding to the opening of the "C" so as to form locking means making it possible to adapt the inflation bandage device to the diameter of the pulmonary artery. The ring also comprises holes for the passage of sutures allowing it to be fixed to the pulmonary artery of the patient. The inflation of this ring leads to the deformation of the thin flexible silicone inside wall in a centripetal direction, which causes a compression of the pulmonary artery and a reduction in its inner diameter. The inflation is carried out using a liquid which is injected using the insufflating button which can also be pulled to allow deflation of the ring.

This type of inflatable vascular ring exists not only in cardiac surgery but also in hepatic surgery. Thus the PCT application WO2010/102661A describes an implant for controlling the blood flow inside a vessel, namely more precisely the portal vein. This control is particularly critical for the success of liver transplants and major hepatectomies. In fact, it is vital for the patient that blood flow in the portal vein just after the transplantation or hepatectomy is not excessive, at the risk of unacceptably damaging the hepatic graft. This phenomenon is known by the name of "Small For Size (SFS)" syndrome. This syndrome occurs in the case of a portal flow rate greater than 260 ml/min per 100 g of liver and/or a portal pressure greater than 20 mm Hg. It causes a lethal alteration of the liver.

The perivascular adjustable implant according to WO2010/102661A comprises an inflatable balloon of open annular shape, arranged inside a non-extendible band. The inflation balloon is connected to an injection chamber by an inflation tube. The non-extendible outer band is equipped with locking means of the ring or vessel. The inflation and the deflation of the annular inner balloon makes it possible to restrict (inflation) or increase (deflation) the inner diameter of the vessel around which the implant is placed. This implant comprises, on the inside of the inflatable balloon, means for measuring the blood pressure inside the vessel. FIGS. 2A to 2D of WO2010/102661A show the change in shape of the inflatable balloon as it is inflated. It appears that the inner wall of the inflatable balloon changes from a circular shape (FIG. 2A) to a shape leaving a passage by growing, which is caused by a bulge in the inflation balloon. It is clear that such a compression of the portal vein is equivalent to crushing, causing a stenosis which leads to turbulences in the blood flow resulting in risks of thrombosis.

This implant according to WO2010/102661A does not therefore allow satisfactory control of the flow rate and/or of the blood pressure inside the vessels, in particular the portal vein. This implant does not provide an effective solution to the problem of SFS syndrome, after a hepatectomy or a liver transplant.

In addition, known implant medical devices require an additional surgery to be removed from the patient.

OBJECTIVES OF THE INVENTION

In this context, the invention proposes a device for controlling the circulation flow rate of a fluid inside a biological duct so as to regulate the flow rate or the blood pressure, which device can be removed in a simple and safe manner.

BRIEF DESCRIPTION OF THE INVENTION

The invention concerns a ring with an adjustable inner diameter, intended to be implanted and closed around a biological duct, preferably a vessel, in order to control the diameter of this duct and thus the flow rate and/or pressure of a fluid circulating in the duct, the ring comprising:
  an outer belt with a constant diameter in a closed position;
  an inner chamber that can be inflated and deflated in the closed position, so as to vary its inner diameter;
  a flexible inflation/deflation tube one end of which is connected to the inner chamber and the other end of which is intended to be connected to inflation means;
  the outer belt and the inner chamber forming open collars, the outer belt being equipped with closing means for closing the ring around the duct;
wherein the closing means comprise two lips capable of being joined to one another and to be separated from one another, after the ring is implanted and closed around a biological duct, by over-inflation of the inner chamber, wherein the lips have contact surfaces facing each other, the closing means comprising at least one perforation arranged on the contact surface of a first of the two lips and at least one protrusion protruding from the contact surface of a second of the two lips, the protrusion and the perforation being configured so that the protrusion is retained in the perforation by fitting, the fitting being selected to be released in the event of overpressure in the ring.

Thanks to these provisions the ring can be easily and rapidly removed from the biological ducts by a mere over-pressure. Over-pressure may be imparted to the inner chamber through the inflation/deflation tube once the treatment the tube is intended for is over.

However, over-pressure may also result in over-pressure within the biological duct. Opening of the ring under such circumstance may improve the safety of the patient.

The inner chamber, at rest and in the closed position, may have a reduced inner diameter corresponding to the smallest reduced diameter required when in use for controlling the diameter of the duct.

These provisions add a pre-strain to the closing means facilitating its opening upon over-pressure.

The ring according to the invention is a remarkable development of the known implantable perivascular rings intended for controlling the blood flow rate, in particular the portal flow rate and/or pressure.

Due to its original structure, this ring proposes a novel type of non-traumatic pneumatic or hydraulic modulation of the flow rate or pressure of the fluid, for example the blood, circulating in the duct, for example a vessel.

This constitutes significant progress towards successful hepatectomies and liver transplants, by offering the practitioner an effective means of combating SFS syndrome.

This ring is moreover secure, reliable, of a reasonable cost and capable of being produced on an industrial scale in compliance with the required quality and productivity standards.

The invention also relates a kit that can be implanted by surgical route, for controlling the flow rate or blood pressure, comprising this ring and an inflation/deflation module intended to be connected to the proximal end of the inflation/deflation tube, in order to allow the in situ injection of an inflation/deflation fluid into the inner chamber or the in situ extraction of an inflation/deflation fluid out of the inner chamber.

Definitions

In the present disclosure, each singular and each plural interchangeably refers to a plural or a singular.

The definitions which are given below by way of examples, are intended to facilitate the interpretation of the present disclosure.

"duct" and "vessel" interchangeably refer to a channel in which a biological fluid circulates, for example blood or lymph.

"closed position" of the ring means that the two ends of the ring are fixed to each other, so that the ring defines a cylinder.

The "at rest" state of the ring means that the pressures inside and outside the inner chamber of the ring are balanced at the ambient atmospheric pressure. When the ring is positioned and closed around the duct, at rest, it is at least partially inflated so that it restricts the diameter of the duct, compresses it and reduces it.

The distal end of the flexible tube is its free end situated outside the body of the patient in whom the implant is put in place, i.e. the free end intended to be connected to the inflation/deflation means.

The proximal end of the flexible tube is the end opposite to its distal end, i.e. the end connected to the ring according to the invention.

By hardness D1, D2, is meant the Shore A hardness of the material(s) constituting the ring.

By the smallest reduced diameter required when in use for controlling the diameter of the duct is meant the inner diameter of the inner chamber at rest, i.e. partially inflated, for which the diameter of the duct Dc, on which the ring is intended to be positioned, is restricted and reduced to a minimal value Dcr with respect to the normal diameter Den (or maximum diameter) that the duct would have in a "normal state" without this ring around it. For each duct to be enclosed, the Dcr value that the duct must reach once the ring is positioned around it is determined. For example, if the duct is the portal vein, the smallest reduced diameter required when in use for controlling the diameter of the portal vein is the inner diameter $\emptyset_{ir}$ of the inner chamber with which the diameter of the portal vein is restricted by 55%, preferably 50% with respect to the natural, normal diameter Den of the portal vein with no restriction. It must obviously be borne in mind that the diameter Dc of the duct can also be reduced if necessary, once the ring is positioned around it, by inflation of the inner chamber of the ring or increased by deflation of the inner chamber. By "normal state", is meant the state of the duct with no restriction and in which the biological fluid circulates at a non-pathological, normal, average biological flow rate. In the normal state, the biological duct has a normal diameter Den, which depends on the biological species, sex and age of the individual.

The fact that the inner chamber, at rest and in the closed position, may have an inner diameter $\emptyset_{ir}$ corresponding to the smallest reduced diameter required when in use for controlling the diameter of the duct, makes it possible to define a shape of the inner chamber, with no invagination, bulge or fold, in which the ring reduces, to a certain level, the diameter of the duct, and therefore the flow rate and/or pressure of the fluid circulating in the duct.

The smallest reduced diameter required for use can be defined by the level of reduction (e.g. expressed as a percentage of reduction) of the diameter of the duct around which the ring is intended to be implanted and locked. This percentage of reduction may correspond to the requirements for use. In particular, as regards the modulation of the flow rate and/or blood pressure, such as in the portal vein, it may be provided that the ring has a $\emptyset_{ir}$ selected in order to reduce by at the most 55%, preferably by at the most 50%, the diameter of the vessel around which the ring is intended to be arranged and locked. Thus, when the ring according to the invention is positioned and closed around the portal vein, at rest and therefore already partially inflated, the ring restricts the diameter of the vein. It reduces this diameter by at the most 55%, preferably 50%. Depending on the requirement and desired treatment of the patient, it is then possible either to further inflate the ring and thus further reduce the diameter of the inner chamber and as a result the diameter of the vein, or to deflate the ring and increase the diameter of the inner chamber and as a consequence the diameter of the vein around which it is positioned.

The percentage reduction is adapted depending on the ducts around which the ring is intended to be put in place and also depending on the aim of the operation and of the positioning of such a ring. Thus, in the case of SFS, it is desirable to reduce the diameter of the portal vein by 55% or even 50%. As a general rule, a human portal vein has a diameter of 15 mm (±5 mm). The ring positioned and closed around the portal vein, in a rest position, i.e. inflated (but not to its maximum) must reduce the diameter to 6.75 mm (±2.25 mm) for a 55% reduction of the diameter of the portal vein.

When the vessel is a vein (flexible wall), the diameter of the vessel is that for which the flow rate of the circulating fluid corresponds to the normal average biological flow rate.

In practice, during a hepatectomy or a liver transplant, the surgeon puts the open ring according to the invention in place around the portal vein, upstream of the liver, and closes this ring by firmly fixing its ends to each other. The portal vein is thus restricted so that its diameter is reduced by at the most 55%, preferably by at the most 50%. The portal diameter considered is, for example, that corresponding to the normal average portal flow rate in humans, namely 700 ml (+/−200 ml) per minute, i.e. approximately 50 ml/min per 100 g of liver, in a healthy individual; or also approximately 260 ml/min per 100 g of liver, in a patient having undergone a major hepatectomy (80% of the liver removed). This flow rate value of approximately 260 ml/min per 100 g of liver corresponds to the maximal value, below which the patient is exposed to SFS syndrome.

The practitioner can choose, as a function of the clinical data at their disposal, to further reduce or to increase the portal diameter by inflation or deflation of the inner chamber, in order to fix the portal flow rate at a value that is desirable for the patient, by gradually bringing this value back to normal, whilst taking the patient's state of health into account.

This procedure could be applied to other medical or non-medical species, for which the positioning of a perivascular ring is prescribed in order to reduce and then optionally increase the intravascular flow rate.

The diameter of the biological duct may be reduced using the ring according to the invention, until the duct is obstructed (clamping of the duct).

Preferably, $Ø_i$ decreases by inflation and increases by deflation.

The fact that the inner chamber of the ring is inflated at rest in the closed position around the duct and, moreover, that its inner diameter a decreases by inflation and increases by deflation, makes it possible to safely and reliably control the flow rate and/or the internal pressure of a fluid circulating in the biological duct/vessel around which the ring is put in place in the closed position, limiting the associated risks of stenosis and thrombosis.

According to a notable feature of the invention, the ring is characterized in that the inner chamber forms no invagination (nor fold), nor bulge and has a "substantially" circular inner shape, in the closed position of the ring, when this inner chamber is inflated. By "substantially" circular is meant, within the meaning of the present disclosure, a closed plane curve, the points of which are at the same distance from the centre with a tolerance of plus or minus 20%, preferably 10%, of $Ø_i$.

As indicated above, the ring may be an open collar which can be defined by at least one of the following features:
(i) the inner chamber forms, at rest and in the non-closed position of the ring, an open collar on an angular sector between 1° and 5°;
(ii) the outer belt forms, at rest and in the non-closed position of the ring, an open collar over an angular sector between 1° and 10°.

These provisions may add a further pre-strain to the closing means facilitating its opening upon over-pressure.

In the preferred embodiment, the open collar has no angular sector but a narrow channel, the ends to be joined in order to close the ring being parallel when the ring is in open position at rest.

In one possible version of the invention, the flexible inflation tube comprises at least one non-return valve.

In order to allow it to be visible to X-rays, it may be useful, according to the invention, for the ring to comprise at least one radio-opaque part, for example a radio-opaque insert.

DETAILED DESCRIPTION OF THE INVENTION

The following description of a preferred embodiment of the ring according to the invention, will highlight other remarkable features.

This detailed description is given with reference to the attached figures in which.

Figure 3:
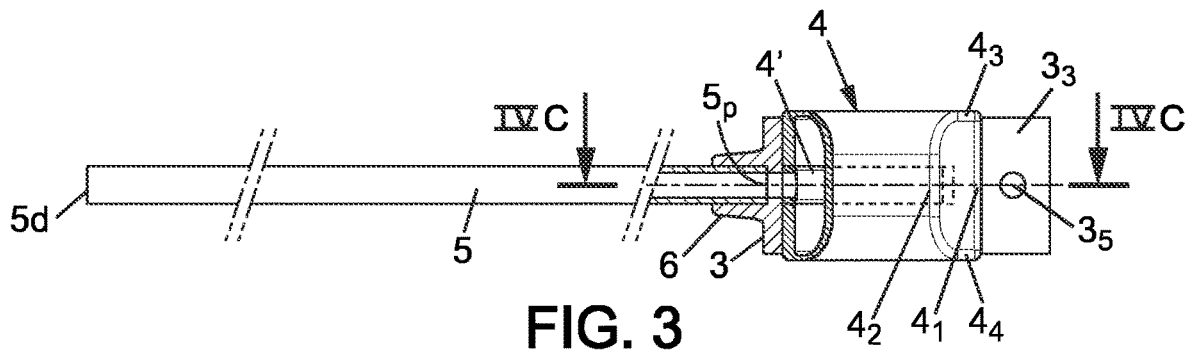
FIG. 3 is a longitudinal cross-sectional view along the cutting plane III-III of FIG. 2A, 2B or 2C.
Figure 4A:
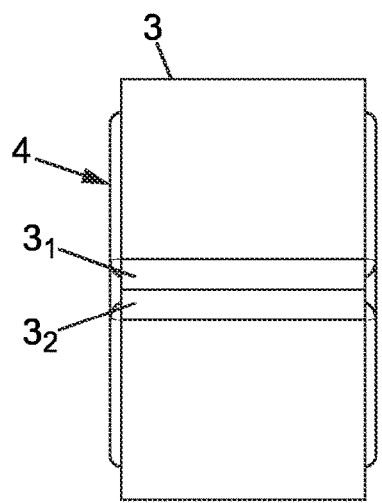
FIGS. 4A & 4B are front views of the ring shown in FIGS. 2A & 2B or 2C respectively.
Figure 4C:
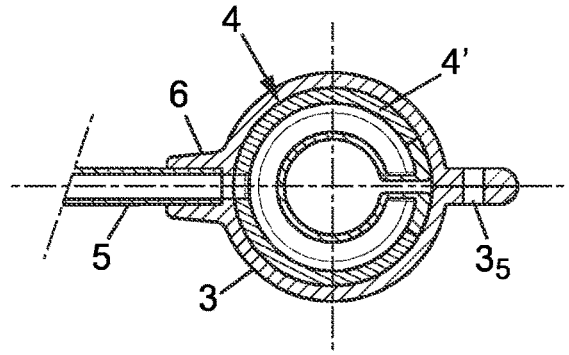
Figure 4B:
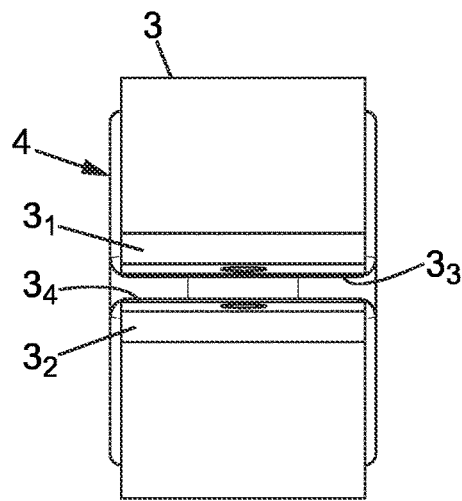
Figure 5A:
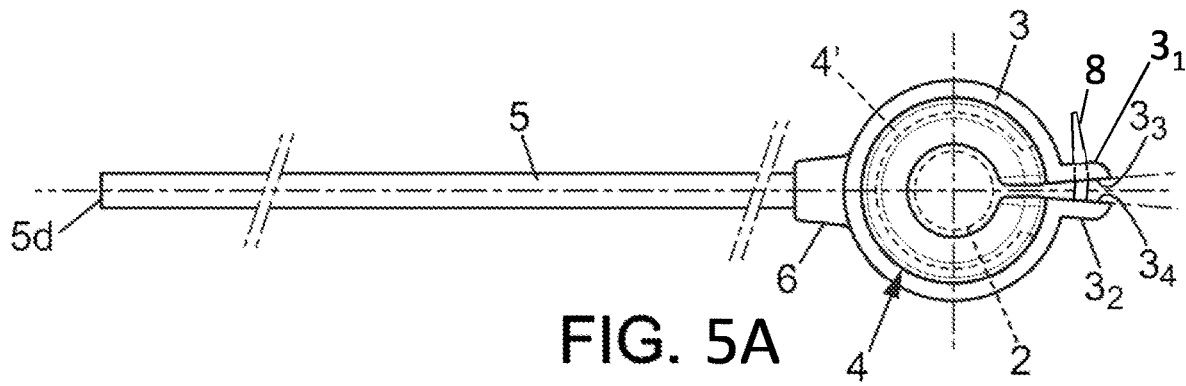
Figure 5B:
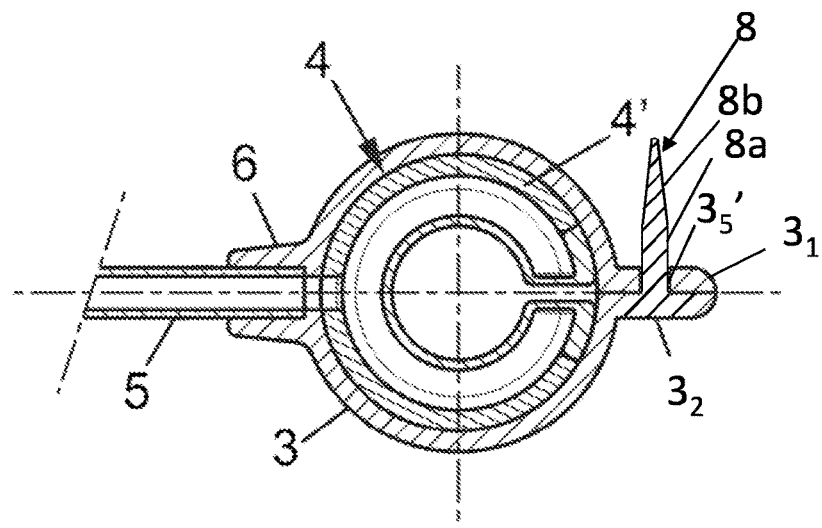

FIG. 4C is a longitudinal cross-sectional view along the cutting plane IV-IV of FIG. 3, FIGS. 5a and 5b are top views of another embodiment of the ring with closing means capable of being separated from one another, after the ring is implanted and closed around a biological duct, by over-inflation of the inner chamber, lips of closing means being joined to one another by a tongue attached to one of the lips and friction fitted in a through hole of the other lip.

Figure 5C:
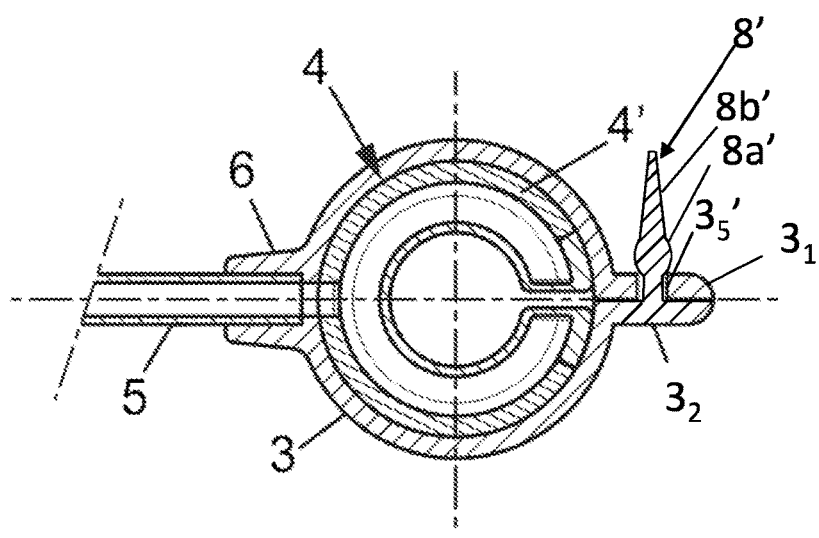

FIG. 5c is a top view of another embodiment of the ring with closing means capable of being separated from one another, after the ring is implanted and closed around a biological duct, by over-inflation of the inner chamber, lips of closing means being joined to one another by a tongue attached to one of the lips and snap fitted in a through hole of the other lip.

As shown in the attached figures the ring (1) according to the invention is a ring that can be inflated and deflated so as to vary its inner diameter ($Ø_i$) so as to be able to compress and release the segment of biological duct for example of blood vessel such as the portal vein, around which said ring (1) is intended to be implanted and closed for controlling the flow circulating in the duct/vessel (2) represented by dot-and-dash lines in the figures.

The ring (1) comprises:
an outer belt (3);
an inner chamber (4) that can be inflated and deflated;
a flexible inflation/deflation tube (5).

Figure 1A:
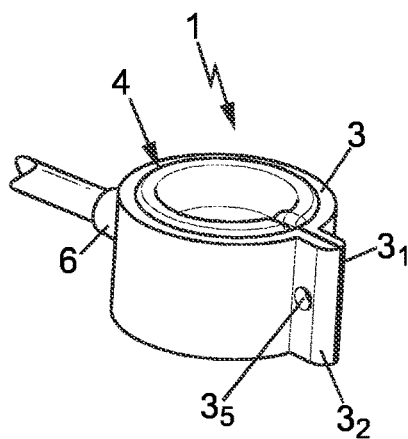
FIGS. 1A & 1B represent perspective views of the ring according to an embodiment, deflated and in the closed and open positions respectively.
Figure 1B:
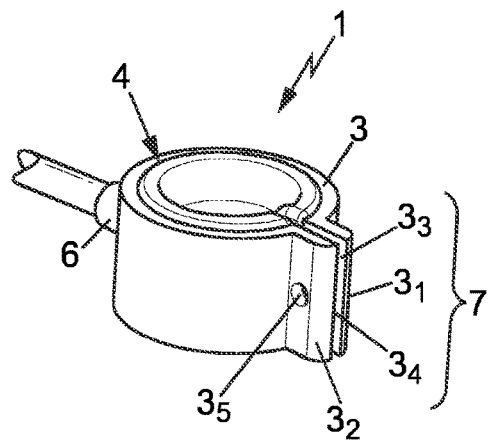
Figure 2A:
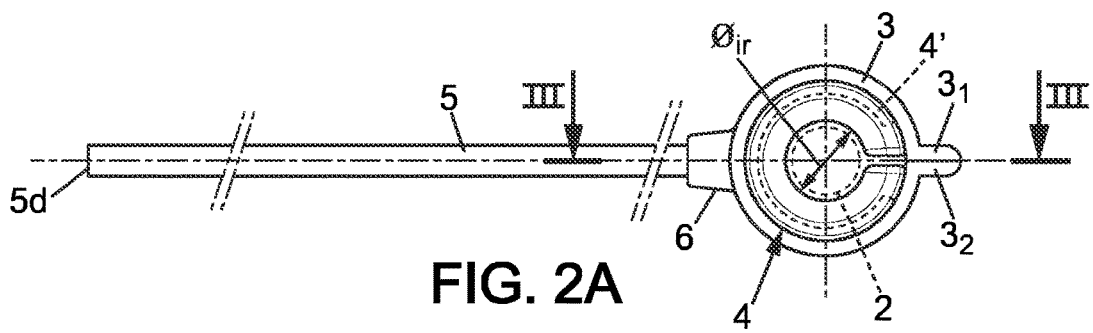
FIGS. 2A, 2B & 2C represent top views of the ring, at rest and respectively in closed (2A) and open positions according to a preferred embodiment (FIG. 2C) and according to an embodiment variant (FIG. 2C), ready to be positioned around the duct.

The outer belt (3) has a substantially constant inner diameter and outer diameter. This outer belt (3) is similar to an open collar (FIGS. 1B, 2B, 2C & 4B) the 2 free ends of which have closing means (7) comprising two outer lips (3₁, 3₂) extending in the centrifugal direction and having faces (3₃, 3₄) opposite one another in the open collar (FIGS. 1B, 2B, 2C & 4B) and in contact with one another in the closed collar (FIGS. 1A, 2A & 4A). As shown in FIGS. 2A, 2B, 2C and 3. These lips (3₁, 3₂) each comprise closing means described in greater details later in order to ensure the closing (FIGS. 1A, 2A & 4A) of the ring (I) after implantation around the vessel (2) the flow rate of which is to be regulated.

This outer belt (3) is made of a semi-rigid material of hardness D1 and selected from the group of biocompatible elastomers, comprising or, even better, constituted by silicone elastomers or analogues.

The inner chamber (4) is an inflatable and deflatable balloon having, at rest and in the closed position (FIG. 2A), a diameter ($Ø_{i,r}$), which may correspond to the minimum diameter value (+/−10%) desired for use, namely a diameter which restricts the diameter Dc of the duct around which it is positioned as soon as it is put in place. In the case of the human portal vein, the normal diameter or maximum value $D_{vpn}$ before reduction is, for example, comprised between 10 mm and 20 mm. The ring put in place and locked around the portal vein has an inner diameter $Ø_{ir}$, which determines a reduction of the portal flow rate preferably by at the most 50%.

Under the effect of the inflation, the inner chamber (4) increases in volume in a centripetal direction, which reduces its inner diameter $Ø_i$. The deflation produces a reduction in the volume of the inner chamber (4), in centrifugal direction, in order to compress or release respectively the vessel (2) of a patient (e.g. portal vein), around which the ring (1) is put in place and closed using the closing means (7).

Figure 2B:
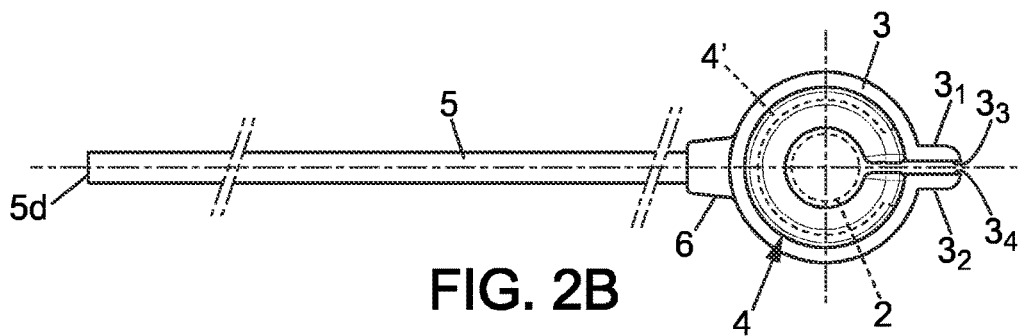

In the embodiment shown in FIG. 2B, the open collar constituted by the outer belt (3) has an opening extending along a narrow channel delimited by the parallel faces $3_3$ and $3_4$ of the outer lips $3_1$ & $3_2$.

Figure 2C:
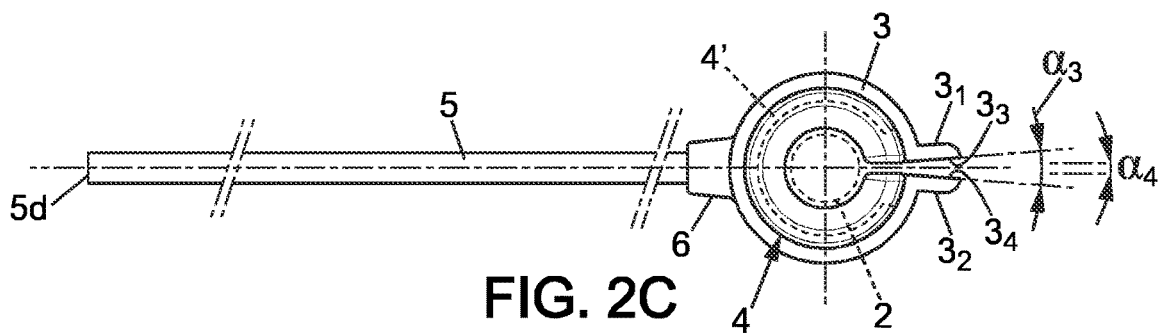

In the preferred embodiment variant shown in FIG. 2C, the open collar constituted by the outer belt (3) has an opening extending over an angular sector $α_3$ comprised between 1° and 10° and preferably equal to approximately 10° in this example. In this variant, the inner chamber (4) is an open collar the ends of which delimit an opening extending over an angular sector c comprised between 1° and 5° and preferably equal to approximately 5°.

As shown by the figures, in particular FIG. 3, this inner chamber (4) is annular and comprises, in the example shown in the drawings (FIG. 3), an outer wall ($4_1$) in contact with and/or firmly fixed to the outer belt (3) and a curved inner wall ($4_2$), the outer wall ($4_1$) and the inner wall ($4_2$) being connected to one another by lateral faces that are substantially straight in the example selected, but which could be curved and are denoted by the reference numbers ($4_3$, $4_4$). The inner chamber (4) could be toroid-shaped according to a variant.

The inner wall ($4_2$) forms the inner edge of this inner chamber (4). This inner edge ($4_2$) has a circular shape, when the ring is at rest (neither inflated: no internal overpressure, nor deflated: no internal low pressure) in the closed position (FIGS. 1A, 2A & 4A), and not arranged around a duct. According to the invention, this circular shape of the inner edge ($4_2$), and, more generally, of the inner chamber (4) is maintained once the ring is arranged around a duct (e.g. vein) and during the inflation and deflation operations. This means that the inner chamber (4) forms no invagination, fold or bulge, either in the rest state, in the inflated state, or in the deflated state. The shape of the inner edge ($4_2$) and, more generally, of the inner chamber (4), remains "substantially" flat and circular, once the ring is arranged around a duct (e.g. vein), from the inflated rest state to a further inflated state and a deflated state corresponding to the requirements of use. In the case of adjustment of the human portal flow rate, these inflated and deflated states are included, for example, within the following inner diameter $Ø_i$ limits (in mm and in increasing order of preference): [5-25]; [6-24]; [7-20].

As shown in FIGS. 2A, 2B, 2C, 3, 4C, a radio-opaque band (4') may be inserted between the inner chamber (4) and the outer belt (3), in the outer wall ($4_2$).

The inner chamber (4) is, for example, made of a flexible material of hardness D2 and selected from the group of biocompatible flexible elastomers comprising or, even better, constituted by silicone elastomers or analogues.

According to a preferred feature of the invention, the hardness D1 of the outer belt (3) is greater than the hardness D2 of the inner chamber (4). For example, D1 is comprised between 60 and 100, preferably 70-90, for example of the order of 80 Shore A. According to another preferred feature of the invention, the hardness D2 of the inner belt (4) is comprised between 5 and 40, preferably 10 and 30, and even more preferably of the order of 20 Shore A.

The flexible inflation/deflation tube (5) is connected by its proximal end ($5p$) to the inside of the inner chamber (4) and by its distal end ($5d$) to inflation means not shown in FIG. 3. The inflation/deflation tube (5) is diametrically opposite the opening of the ring (1) as can be seen in FIGS. 1A, 1B, 2A, 2B, 2C, 3 and 4C. The outer belt (3) has an end piece (6) which extends towards the outside and which receives the proximal end ($5p$) of the inflation tube (5). This inflation tube (5) can be equipped with a plastic non-return valve.

The inflation tube (5) can be made of the same material as the inner chamber (4), for example, with a hardness D3 comprised between D1 and D2, e.g. of the order of 60 Shore A.

The inflation/deflation means (not shown in the drawings) are constituted for example by a syringe, preferably a screw syringe making it possible to make precise inflation/deflation adjustments by injection/tapping of the inflation/deflation fluid.

The ring (1) according to the invention can be put in place around the vessel (2) by the standard surgical route (laparotomy) or by the coelioscopic route. The closing of the ring (1) is carried out by closing means (7). The ring (1) thus positioned has a reduced inner diameter ($Ø_{ir}$) which restricts the vessel (2) to the smallest reduced diameter required for use (Dvpr) and thus limits the flow rate or pressure, for example blood, to a given level dependent on $Ø_{ir}$. The practitioner then proceeds to adjust the flow rate and/or pressure, by inflation/deflation. In the case of hepatectomy or liver transplant, this adjustment aims to maintain an intrahepatic pressure less than or equal to 20 mm Hg, preferably 15 mm Hg. $Ø_i$ is gradually increased by deflation. $D_{vp}$ and with it the flow rate and/or the blood pressure in the portal vein therefore also increase(s) gradually, until $D_{vp}$ reaches $D_{vpn}$ (normal diameter or maximum diameter of the portal vein). The time taken for this rise of $D_{vpr}$ to $D_{vpn}$ is that which is necessary for hepatic parenchyma in order to recover a capacity to contain the intrahepatic pressure below 20 mm Hg, preferably below 15 mm Hg, for the pressure and/or the flow rate downstream of the ring, corresponding to a portal diameter equal to $D_{vpn}$.

This significantly limits the risks of SFS syndrome for the patient.

The ring according to the invention, once closed by the closing means, can be reopened by over-inflation of the inner chamber, which causes the closing means to be spaced apart from each other. After opening the ring (1), the practitioner can also take advantage of the over-inflation of the ring (1), in order to keep the free ends of the ring (1) apart from each other and thus facilitate its extraction. This has the advantage of avoiding further anaesthesia and its associated risks.

FIGS. 5A, 5B and 5C show embodiments of the ring according to the invention wherein the lips of the closing means are capable of being separated from one another, after the ring is implanted and closed around a biological duct, by over-inflation of the inner chamber.

In the embodiment illustrated on FIGS. 5A and 5B, the closing means comprise one perforation $3_5'$ arranged on the face $3_3$, forming a contact surface, of a first $3_1$ of the lips and one protrusion 8 protruding from the face $3_4$, forming a contact surface, of a second $3_2$ of the lips. In particular, the perforation $3_5'$ is a through hole, for example of circular cross-section, formed in the first lip $3_1$ and the protrusion 8 is a tongue extending from the contact surface $3_4$ of the second lip $3_2$. As previously mentioned, the first $3_1$ and second $3_2$ lips are formed of deformable material, and especially elastomeric material, such as silicone. The tongue is made in one piece with the second lip $3_2$ so as to be elastically deformable. The tongue is for example cylindrical of circular cross-section and has a length measured perpendicularly to the second lip $3_2$ from which it extends. The tongue comprise a fitting portion 8a attached to the contact surface face $3_4$ of the second lip $3_2$ and sized, in terms of diameter and length, to be retained in the through hole of the first lip $3_1$ by friction fitting. The friction fitting resulting from the combination of sizes and material is selected to be released in the event of overpressure in the ring.

The tongue is also provided with an extension adjacent the fitting portion 8a opposite the second lip $3_2$. The extension has a conical shape with a diameter reducing from the base adjacent the fitting portion 8a to a tip. The extension provides an extra-length able to pass through the perforation $3_5'$ and thereby forms a grasping portion 8b enabling the used to grasp the tongue so as to pull the fitting portion 8a within the perforation $3_5'$.

The tongue and the through hole could have any other suitable cross section, preferably complementary to one another.

The embodiment illustrated on FIG. 5C differs from that of FIGS. 5A and 5B in that the tongue 8' comprises an enlarged portion 8a' sized to rest on a surface of the first lip $3_1$ opposite the contact face of the first lip $3_1$ when the ring is closed, thereby providing a snap-fitting. The enlarged portion has a transverse dimension greater than that of the through hole and, in particular, a transverse dimension that is 5% to 20% greater than that of the through hole. In the illustrated embodiment, the fitting portion of the tongue 8' attached to the contact surface of the second lip $3_2$ is narrower that the through hole of the first lip $3_1$. The fitting portion may then be arranged within in the through hole without contacting walls of the through hole. However, the fitting portion could be otherwise configured so as to provide a friction fitting with the through hole.

As in the embodiment of FIGS. 5A and 5B, the tongue 8' may comprise a grasping portion adjacent the fitting portion opposite the second lip $3_2$.

The invention is not limited to the disclosed tongues and through holes. The closing means could comprise any other kind of protrusion and perforation configured so that the protrusion is retained in the perforation by fitting such as force fitting, friction fitting, snap fitting and others, the fitting being selected to be released in the event of overpressure in the ring.

The invention claimed is:

1. A ring with an adjustable inner diameter, intended to be implanted and closed around a biological duct, in order to control a diameter of the biological duct and thus a flow rate and/or pressure of a fluid circulating in the biological duct, this ring comprising:
   an outer belt with a constant diameter in a closed position;
   an inner chamber that can be inflated and deflated in the closed position, so as to vary an inner diameter thereof;
   a flexible inflation/deflation tube, one end of which is connected to the inner chamber and the other end of which is intended to be connected to inflation means;
   the outer belt and the inner chamber forming open collars, the outer belt being equipped with closing means for closing the ring around the biological duct;
   wherein the closing means comprise two lips capable of being joined to one another and to be separated from one another, after the ring is implanted and closed around the biological duct, by over-inflation of the inner chamber,
   wherein the lips have contact surfaces facing each other, the closing means comprising at least one perforation arranged on the contact surface of a first of the two lips and at least one protrusion protruding from the contact surface of a second of the two lips, the protrusion and the at least one perforation being configured so that the protrusion is retained in the at least one perforation by fitting, the fitting being selected to be released in the event of overpressure in the ring.

2. The ring according to claim 1, wherein the inner chamber, at rest and in the closed position, has a reduced inner diameter corresponding to a smallest reduced diameter required when in use for controlling the diameter of the biological duct.

3. The ring according to claim 1, wherein the at least one perforation is a through hole formed in the first lip and the protrusion is a tongue comprising a fitting portion attached to the contact surface of the second lip and sized to be retained in the through hole by friction fitting.

4. The ring according to claim 3, wherein the tongue comprises a grasping portion adjacent the fitting portion opposite the second lip, the grasping portion being sized to pass through the through hole and to be grasped by a user.

5. The ring according to claim 1, wherein the at least one perforation is a through hole formed in the first lip and the protrusion is a tongue, the tongue comprising a fitting portion attached to the contact surface of the second lip and sized to be arranged within the through hole, and an enlarged portion sized to rest on a surface of the first lip opposite a contact face of the first lip.

6. The ring according to claim 5, wherein the tongue comprises a grasping portion adjacent the fitting portion opposite the second lip, the grasping portion being sized to pass through the through hole and to be grasped by a user.

7. The ring according to claim 1, wherein the inner chamber has no invagination at rest and, in the closed position of the ring, an inner edge of the inner chamber intended to be in contact with the duct has a substantially circular shape.

8. The ring according to claim 1, wherein the inner diameter of the inner chamber decreases by inflation and increases by deflation.

9. The ring according to claim 1, wherein the lips extend in the centrifugal direction.

10. The ring according to claim 1, comprising at least one radio-opaque part.

11. The ring according to claim 1, wherein the inner chamber forms, at rest and in a non-closed position of the ring, an open collar on an angular sector less than or equal to 5° and the outer belt forms, at rest and in the non-closed position of the ring, an open collar over an angular sector less than or equal to 10°.

12. A kit that can be implanted by surgical route, allowing an adjustment of an inner diameter of a biological duct and thus a flow rate of a fluid circulating in the biological duct, the kit comprising:
   * a ring according to claim 1;
   * an inflation/deflation module intended to be connected to a distal end of the flexible inflation/deflation tube, in order to allow the in situ injection of an inflation/deflation fluid into the inner chamber or the in situ extraction of an inflation/deflation fluid out of the inner chamber.

* * * * *